United States Patent [19]
Bresnaham et al.

[11] Patent Number: 6,117,105
[45] Date of Patent: Sep. 12, 2000

[54] AORTIC CATHETER AND METHODS FOR INDUCING CARDIOPLEGIC ARREST AND FOR SELECTIVE AORTIC PERFUSION

[75] Inventors: John F. Bresnaham, Rochester, Minn.; John A. Macoviak, La Jolla, Calif.; Wilfred J. Samson, Saratoga, Calif.; Steve G. Baker, Sunnyvale, Calif.; Karl Van Dyk, Freemont, Calif.

[73] Assignee: Cardeon Corporation, Cupertino, Calif.

[21] Appl. No.: 09/205,753

[22] Filed: Dec. 4, 1998

Related U.S. Application Data

[60] Provisional application No. 60/067,945, Dec. 8, 1997, abandoned.

[51] Int. Cl.$^7$ .................................................. A61M 29/00
[52] U.S. Cl. ..................... 604/96.01; 604/500; 604/509
[58] Field of Search ............... 604/96, 101, 500, 604/508, 509, 523, 532; 606/192–194

[56] References Cited

U.S. PATENT DOCUMENTS

| | | | |
|---|---|---|---|
| 4,943,277 | 7/1990 | Bolling | 604/96 |
| 5,295,958 | 3/1994 | Shturman | 606/101 |
| 5,308,320 | 5/1994 | Safar et al. | 604/4 |
| 5,312,344 | 5/1994 | Grinfeld et al. | 604/101 |
| 5,334,142 | 8/1994 | Paradis | 604/53 |
| 5,383,854 | 1/1995 | Safar et al. | 604/98 |
| 5,395,331 | 3/1995 | O'Neill et al. | 604/96 |
| 5,413,558 | 5/1995 | Paradis | 604/101 |
| 5,423,745 | 6/1995 | Todd et al. | 604/53 |
| 5,433,700 | 7/1995 | Peters | 604/4 |
| 5,437,633 | 8/1995 | Manning | 604/53 |
| 5,443,446 | 8/1995 | Shturman | 604/49 |
| 5,451,207 | 9/1995 | Yock | 604/53 |
| 5,458,574 | 10/1995 | MacHold et al. | 604/101 |
| 5,496,277 | 3/1996 | Termin et al. | 604/104 |
| 5,536,251 | 7/1996 | Evard et al. | 604/93 |
| 5,584,803 | 12/1996 | Stevens et al. | 604/4 |
| 5,599,329 | 2/1997 | Gabbay | 604/284 |
| 5,678,570 | 10/1997 | Manning | 128/897 |
| 5,697,905 | 12/1997 | d'Ambrosio | 604/96 |
| 5,702,368 | 12/1997 | Stevens et al. | 604/171 |
| 5,716,318 | 2/1998 | Manning | 600/16 |
| 5,725,496 | 3/1998 | Peters | 604/49 |
| 5,738,649 | 4/1998 | Macoviak | 604/43 |
| 5,755,687 | 5/1998 | Donlon | 604/53 |
| 5,755,784 | 5/1998 | Jarvik | 623/3 |
| 5,759,170 | 6/1998 | Peters | 604/4 |
| 5,766,151 | 6/1998 | Valley et al. | 604/96 |
| 5,769,812 | 6/1998 | Stevens et al. | 604/4 |

(List continued on next page.)

FOREIGN PATENT DOCUMENTS

| | | |
|---|---|---|
| 86201487 | 8/1986 | European Pat. Off. . |
| 0 604 803 | 7/1994 | European Pat. Off. . |
| 0 709 108 | 5/1996 | European Pat. Off. . |
| 83-813285/45 | 7/1983 | U.S.S.R. . |
| 85-037128/06 | 7/1984 | U.S.S.R. . |

OTHER PUBLICATIONS

Technical Specifications Percluder® aortic occluding balloon, Datascope Corp. © 1987 Datascope Corp.

*Primary Examiner*—John D. Yasko
*Attorney, Agent, or Firm*—Fulwider Patton Lee & Utecht, LLP

[57] ABSTRACT

The present invention provides an aortic catheter having an upstream occlusion member positioned in the ascending aorta between the coronary arteries and the brachiocephalic artery and a downstream anchoring member positioned in the descending aorta, downstream of the aortic arch. The upstream occlusion member may be an inflatable balloon or a selectively deployable external catheter valve. The downstream anchoring member may be a larger inflatable balloon or other anchoring structure that provides sufficient friction to prevent migration of the balloon catheter in the upstream or downstream direction. In addition, an arch perfusion lumen, a corporeal perfusion lumen and a cardioplegia lumen are provided for performing selective perfusion and cardioplegic arrest.

25 Claims, 12 Drawing Sheets

U.S. PATENT DOCUMENTS

| | | | |
|---|---|---|---|
| 5,776,190 | 7/1998 | Jarvik | 623/3 |
| 5,792,094 | 8/1998 | Stevens et al. | 604/4 |
| 5,795,325 | 8/1998 | Valley et al. | 604/53 |
| 5,800,375 | 9/1998 | Sweezer et al. | 604/4 |
| 5,814,016 | 9/1998 | Valley et al. | 604/96 |
| 5,820,593 | 10/1998 | Safar et al. | 604/96 |
| 5,827,237 | 10/1998 | Macoviak et al. | 604/246 |
| 5,833,671 | 11/1998 | Macoviak et al. | 604/247 |
| 5,840,081 | 11/1998 | Andersen et al. | 623/2 |
| 5,846,260 | 12/1998 | Maahs | 606/200 |
| 5,906,588 | 5/1999 | Safar et al. | 604/64 |

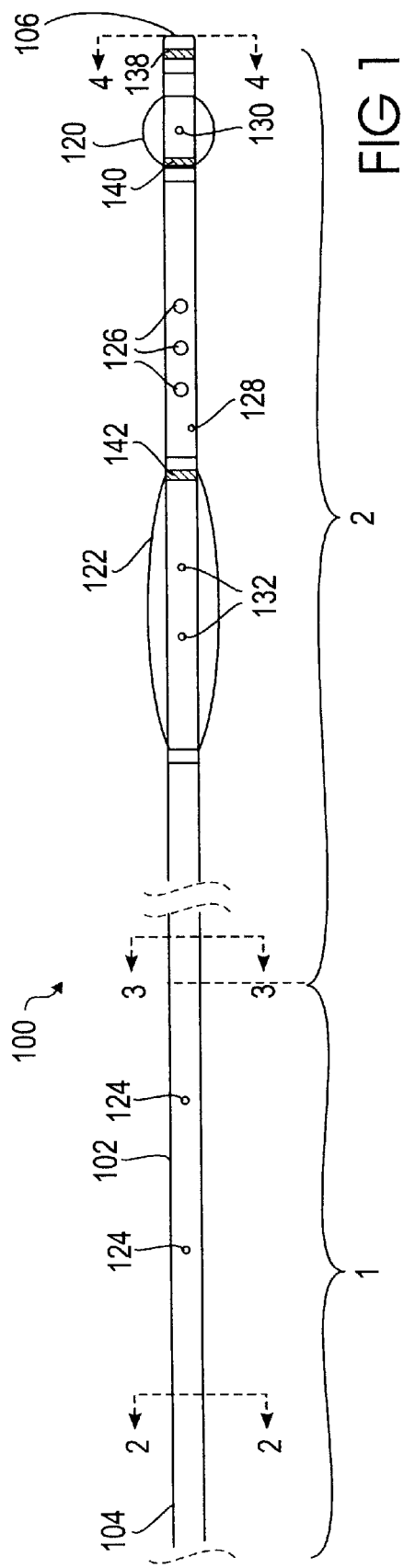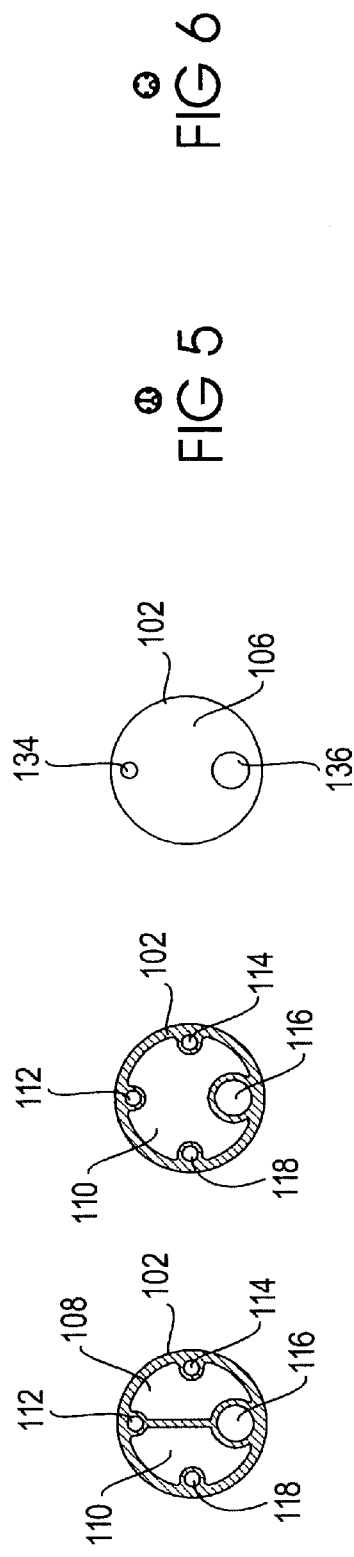

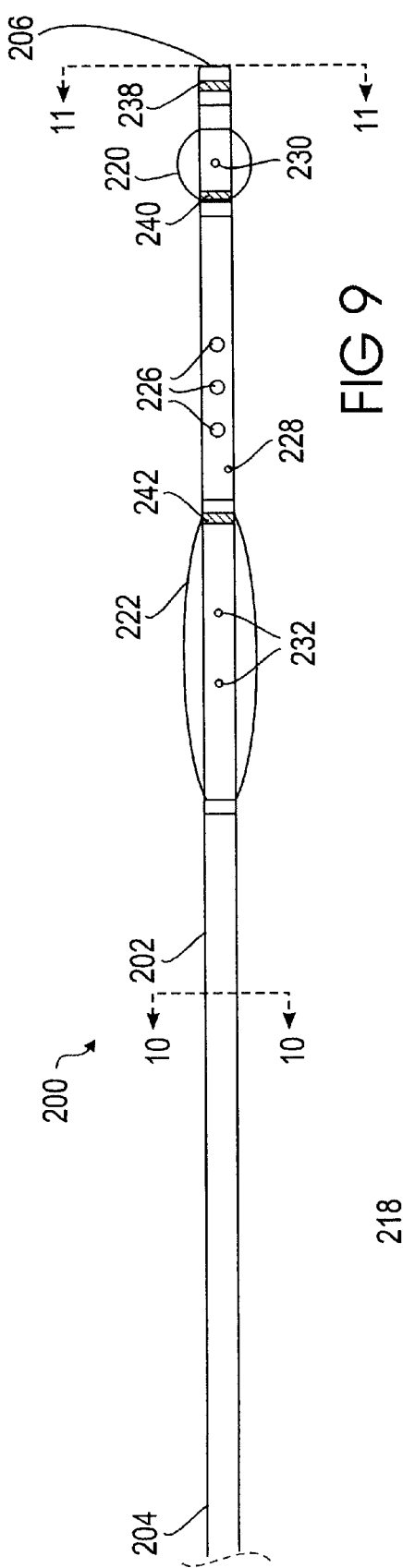

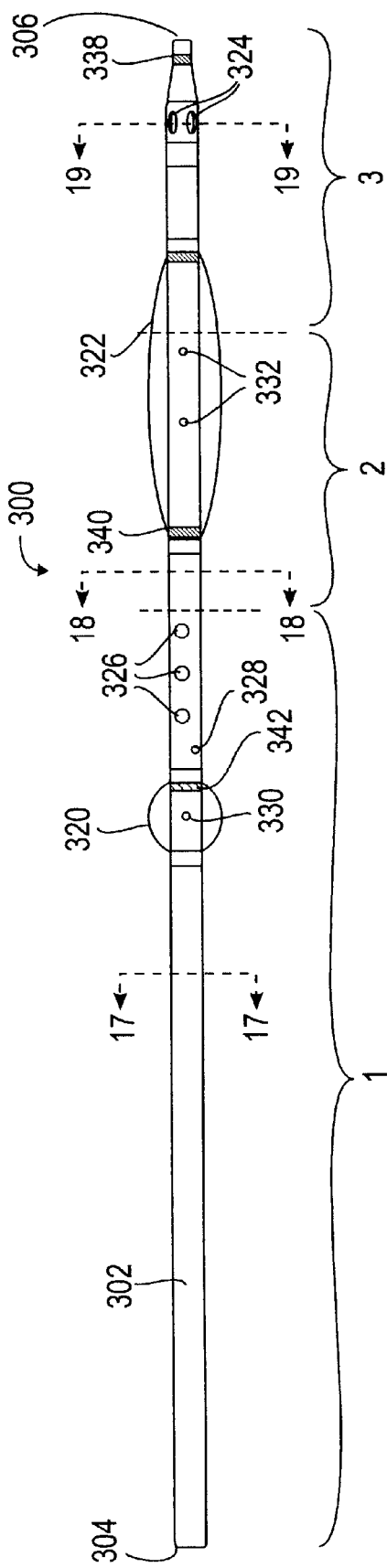
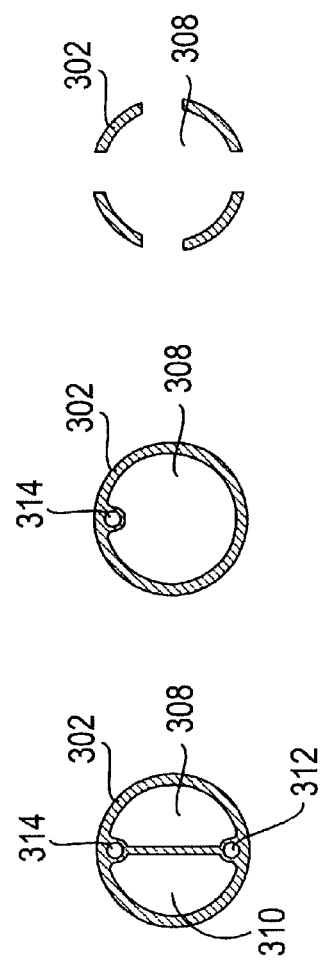

AORTIC CATHETER AND METHODS FOR INDUCING CARDIOPLEGIC ARREST AND FOR SELECTIVE AORTIC PERFUSION

FIELD OF THE INVENTION

This application claims the benefit of U.S. Provisional Patent Application serial No. 60/067,945 filed on Dec. 08, 1997, now abandoned the specification of which is hereby incorporated by reference in its entirety.

The present invention relates to an aortic catheter for inducing cardioplegic arrest and for segmenting and selectively perfusing the aorta during cardiopulmonary bypass.

BACKGROUND OF THE INVENTION

Recent advances in the field of minimally invasive cardiac surgery have included the development of aortic catheters and methods for inducing cardioplegic arrest without the necessity of opening the patient's chest with a sternotomy or other major thoracotomy. For example, U.S. Pat. No. Re 35,352 to Peters describes a single balloon catheter for occluding a patient's ascending aorta and a method for inducing cardioplegic arrest. A perfusion lumen or a contralateral arterial cannula is provided for supplying oxygenated blood during cardiopulmonary bypass. U.S. Pat. No. 5,584,803 to Stevens et al. describes a single balloon catheter for inducing cardioplegic arrest and a system for providing cardiopulmonary support during closed chest cardiac surgery. A coaxial arterial cannula is provided for supplying oxygenated blood during cardiopulmonary bypass. The occlusion balloon of these catheters must be very carefully placed in the ascending aorta between the coronary arteries and the brachiocephalic artery, therefore the position of the catheter must be continuously monitored to avoid complications. In clinical use, these single balloon catheters have shown a tendency to migrate in the direction of the pressure gradient within the aorta. That is to say that, during infusion of cardioplegia, the balloon catheter will tend to migrate downstream due to the higher pressure on the upstream side of the balloon and, when the CPB pump is on, the balloon catheter with tend to migrate upstream into the aortic root due to the higher pressure on the downstream side of the balloon. This migration can be problematic if the balloon migrates far enough to occlude the brachiocephalic artery on the downstream side or the coronary arteries on the upstream side. PCT patent application WO 97/21462 by Fan et al. attempts to overcome this problem with a balloon catheter having high friction areas on the outer surface of the balloon. A problem with this single balloon approach is that a relatively large balloon is needed to create enough friction to avoid migration of the inflated balloon. The larger the balloon is, the more carefully it must be placed in the ascending aorta to avoid occluding the coronary arteries or the brachiocephalic artery and the less margin of error there is should any balloon migration occur.

U.S. Pat. No 5,312,344 to Grinfeld et al. describes an arterial perfusion cannula having two closely spaced balloons positioned in the ascending aorta. However, this patent does not provide any guidance on how to avoid migration or inadvertent occlusion of the coronary arteries or the brachiocephalic artery. It would be desirable to provide an aortic occlusion catheter for inducing cardioplegic arrest that minimizes the likelihood of migration of the balloon or occluding member in the ascending aorta.

Another important development in the area of aortic balloon catheters is the concept of selective aortic perfusion. U.S. Pat. Nos. 5,308,320, 5,383,854 and 5,820,593 by Peter Safar, S. William Stezoski and Miroslav Klain describe a double balloon catheter for segmenting a patient's aorta for selective perfusion of different organ systems within the body. Other U.S. patents which address the concept of selective aortic perfusion include U.S. Pat. Nos.; 5,738,649, 5,833,671 and 5,827,237 by John A. Macoviak; and Michael Ross and commonly owned, copending patent applications Ser. No.; 08/909,293 filed Aug. 11, 1997; and Ser. No. 08/909,380 filed Nov. 8, 1997, by Safar et al.; and Ser. No. 08/665,635, filed Jun. 18, 1996 by John A. Macoviak; and Michael Ross. These patent applications and all other patents referred to herein are hereby incorporated by reference in their entirety. Selective perfusion can be used to prioritize the flow of oxygenated blood or other protective fluids to the various organ systems, therefore achieving optimal preservation of all organ systems within the body. It would be desirable to include this feature of selective perfusion in an aortic occlusion catheter for inducing cardioplegic arrest.

SUMMARY OF THE INVENTION

Accordingly, the present invention provides an aortic catheter having an upstream occlusion member positioned in the ascending aorta between the coronary arteries and the brachiocephalic artery and a downstream anchoring member positioned in the descending aorta, downstream of the aortic arch. The upstream occlusion member may be an inflatable balloon or a selectively deployable external catheter valve. Preferably, the upstream occlusion member is narrow enough in construction that it is easily placed between the coronary arteries and the brachiocephalic artery without any danger of inadvertently occluding either. The downstream anchoring member may be a larger inflatable balloon or other anchoring structure that provides sufficient friction to prevent migration of the balloon catheter in the upstream or downstream direction. Preferably, the upstream occlusion member and the downstream anchoring member are mounted on an elongated catheter shaft, which includes lumens for inflating or otherwise actuating the occlusion member and the anchoring member and a lumen or lumens for perfusion of the aorta with oxygenated blood or other fluids. The catheter may be configured for retrograde deployment via a peripheral artery, such as the femoral artery, or it may be configured for antegrade deployment via an aortotomy incision or direct puncture in the ascending aorta.

A first embodiment of the aortic catheter of the present invention is described, which is configured for retrograde deployment via a peripheral artery, such as the femoral artery. The aortic catheter has an elongated catheter shaft having a proximal end and a distal end. An upstream occlusion member, in the form of an inflatable balloon, is mounted on the catheter shaft near the distal end of the catheter shaft so that it is positioned in the ascending aorta when deployed. A larger inflatable balloon, which serves as a downstream anchoring member, is mounted at a position proximal to the upstream occlusion member so that it is positioned in the descending aorta when deployed. A corporeal perfusion lumen extends through the catheter shaft from the proximal end to one or more corporeal perfusion ports on the exterior of the catheter shaft proximal of the downstream anchoring member. An arch perfusion lumen extends through the catheter shaft from the proximal end to one or more arch perfusion ports on the exterior of the catheter shaft between the upstream occlusion member and the downstream anchoring member. An arch pressure lumen extends through the catheter shaft from the proximal end to an arch pressure port located between the upstream occlusion member and the downstream anchoring member to monitor pressure in the aortic arch. A common balloon inflation lumen extends through the catheter shaft from the proximal end to balloon inflation ports within the upstream occlusion member and the downstream anchoring member. A root pressure lumen extends through the catheter shaft from the proximal end to a root pressure port near the distal end of the catheter shaft to monitor pressure in the aortic root. A guide wire and cardioplegia lumen extends from the proximal end of the catheter shaft to the distal end, distal to the upstream occlusion member.

A second embodiment of the aortic catheter is described, which is also configured for retrograde deployment via a peripheral artery, such as the femoral artery. The aortic catheter has an elongated catheter shaft having a proximal end and a distal end. An upstream occlusion member, in the form of an inflatable balloon, is mounted on the catheter shaft near the distal end of the catheter shaft so that it is positioned in the ascending aorta when deployed. A larger inflatable balloon, which serves as a downstream anchoring member, is mounted at a position proximal to the upstream occlusion member so that it is positioned in the descending aorta when deployed. An arch perfusion lumen extends through the catheter shaft from the proximal end to one or more arch perfusion ports on the exterior of the catheter shaft between the upstream occlusion member and the downstream anchoring member. An arch pressure lumen extends through the catheter shaft from the proximal end to an arch pressure port located between the upstream occlusion member and the downstream anchoring member to monitor pressure in the aortic arch. A common balloon inflation lumen extends through the catheter shaft from the proximal end to balloon inflation ports within the upstream occlusion member and the downstream anchoring member. A root pressure lumen extends through the catheter shaft from the proximal end to a root pressure port near the distal end of the catheter shaft to monitor pressure in the aortic root. A guide wire and cardioplegia lumen extends from the proximal end of the catheter shaft to the distal end, distal to the upstream occlusion member. A separate contralateral or coaxial arterial cannula would be used with this embodiment of the aortic catheter to supply oxygenated blood to the corporeal circulation.

A third embodiment of the aortic catheter of the present invention is described, which is configured for antegrade deployment via an aortotomy or direct aortic puncture. The aortic catheter has an elongated catheter shaft having a proximal end and a distal end. Because the catheter is configured for antegrade deployment, the proximal and distal positions of many of the features of the catheter are reversed with respect to the retrograde embodiments previously described. A downstream anchoring member, in the form of a large inflatable balloon, is mounted on the catheter shaft near the distal end of the catheter shaft so that it is positioned in the descending aorta when deployed. An upstream occlusion member, in the form of an inflatable balloon, is mounted at a position proximal to the downstream anchoring member so that it is positioned in the ascending aorta when deployed. An arch perfusion lumen extends through the catheter shaft from the proximal end to one or more arch perfusion ports on the exterior of the catheter shaft between the upstream occlusion member and the downstream anchoring member. An arch pressure lumen extends through the catheter shaft from the proximal end to an arch pressure port located between the upstream occlusion member and the downstream anchoring member to monitor pressure in the aortic arch. A common balloon inflation lumen extends through the catheter shaft from the proximal end to balloon inflation ports within the upstream occlusion member and the downstream anchoring member. A guide wire and corporeal perfusion lumen extends from the proximal end of the catheter shaft to the distal end, distal to the downstream anchoring member. A separate cardioplegia needle or catheter would be used with this embodiment of the aortic catheter to infuse cardioplegia fluid into the aortic root upstream of the upstream occlusion member.

A fourth embodiment of the aortic catheter, configured for retrograde deployment, is described wherein the upstream occlusion member is in the form of a narrow, disk shaped balloon. A fifth embodiment of the aortic catheter, configured for antegrade deployment, is described wherein the upstream occlusion member is in the form of a narrow, disk shaped balloon.

A sixth embodiment of the aortic catheter, configured for retrograde deployment, is described wherein the upstream occlusion member is in the form of a selectively deployable peripheral flow external catheter valve. A seventh embodiment of the aortic catheter, also configured for retrograde deployment, is described wherein the upstream occlusion member is in the form of a selectively deployable central flow external catheter valve. An eighth embodiment of the aortic catheter, configured for retrograde deployment, is described wherein the downstream anchoring member is in the form of two inflatable balloons.

Methods according to the present invention are described using the aortic catheter for occluding the ascending aorta and for inducing cardioplegic arrest, for supporting the patient's circulation on cardiopulmonary bypass, for partitioning the patient's aorta and for performing selective aortic perfusion.

BRIEF DESCRIPTION OF THE DRAWINGS

FIG. 1 shows a side view of a first embodiment of the aortic catheter of the present invention configured for retrograde deployment via a peripheral artery access, such as the femoral artery.

FIG. 2 is a magnified lateral cross section of the aortic catheter of FIG. 1 taken along line 2—2 in FIG. 1.

FIG. 3 is a magnified lateral cross section of the aortic catheter of FIG. 1 taken along line 3—3 in FIG. 1.

FIG. 4 is a magnified distal view of the aortic catheter of FIG. 1 taken along line 4—4 in FIG. 1.

FIG. 5 is a full scale drawing of the lateral cross section taken along line 2—2 in FIG. 1 showing the actual size of a catheter with a 10.5 French (3.5 mm) outer diameter.

FIG. 6 is a full scale drawing of the lateral cross section taken along line 3—3 in FIG. 1 showing the actual size of a catheter with a 10.5 French (3.5 mm) outer diameter.

FIG. 7 is a full scale drawing of the lateral cross section taken along line 2—2 in FIG. 1 showing the actual size of a catheter with a 12 French (4.0 mm) outer diameter.

FIG. 8 is a full scale drawing of the lateral cross section taken along line 3—3 in FIG. 1 showing the actual size of a catheter with a 12 French (4.0 mm) outer diameter.

FIG. 9 shows a side view of a second embodiment of the aortic catheter of the present invention configured for retrograde deployment via a peripheral artery access, such as the femoral artery.

FIG. 10 is a magnified lateral cross section of the aortic catheter of FIG. 9 taken along line 10—10 in FIG 9.

FIG. 11 is a magnified lateral distal view of the aortic catheter of FIG. 9 taken along line 11—11 in FIG. 9.

FIG. 12 is a full scale drawing of the lateral cross section taken along line 10—10 in FIG. 9 showing the actual size of a catheter with a 10.5 French (3.5 mm) outer diameter.

FIG. 13 is a full scale drawing of the lateral cross section taken along line 11—11 in FIG. 9 showing the actual size of a catheter with a 12 French (4.0 mm) outer diameter.

FIG. 16 shows a side view of a third embodiment of the aortic catheter according to the present invention with a catheter shaft configured for antegrade deployment via an aortotomy incision in the ascending aorta.

FIG. 17 is a magnified lateral cross section of the aortic catheter of FIG. 16 taken along line 17—17 in FIG. 16.

FIG. 18 is a magnified lateral cross section of the aortic catheter of FIG. 16 taken along line 18—18 in FIG. 16.

FIG. 19 is a magnified lateral cross section of the aortic catheter of FIG. 16 taken along line 19—19 in FIG. 16.

FIG. 20 is a full scale drawing of the lateral cross section taken along line 17—17 in FIG. 16 showing the actual size of a catheter with a 10.5 French (3.5 mm) outer diameter.

FIG. 21 is a full scale drawing of the lateral cross section taken along line 18—18 in FIG. 16 showing the actual size of a catheter with a 10.5 French (3.5 mm) outer diameter.

FIG. 22 is a full scale drawing of the lateral cross section taken along line 17—17 in FIG. 16 showing the actual size of a catheter with a 12 French (4.0 mm) outer diameter.

FIG. 23 is a full scale drawing of the lateral cross section taken along line 18—18 in FIG. 16 showing the actual size of a catheter with a 12 French (4.0 mm) outer diameter.

DETAILED DESCRIPTION OF THE INVENTION

Figure 14:
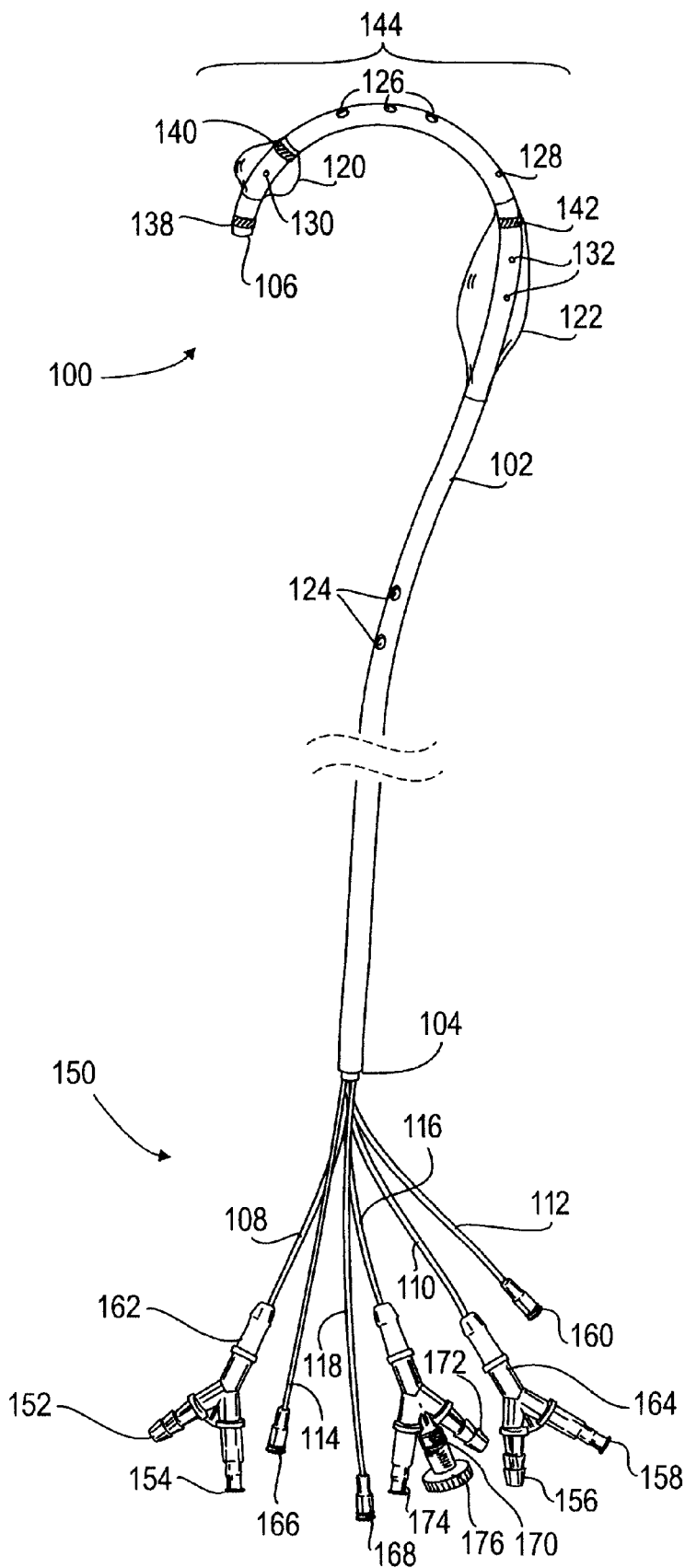
FIG. 14 shows a side view of an aortic catheter according to the present invention with a catheter shaft configured for retrograde deployment via femoral artery access.

FIGS. 1 through 8 illustrate the shaft portion of a first embodiment of the aortic catheter 100 of the present invention, which is configured for retrograde deployment via a peripheral artery, such as the femoral artery. FIG. 1 is a side view of the shaft portion of the aortic catheter 100. FIG. 2 is a magnified lateral cross section of the aortic catheter 100 taken along line 2—2 in FIG. 1. FIG. 3 is a magnified lateral cross section of the aortic catheter 100 taken along line 3—3 in FIG. 1. FIG. 4 is a magnified distal end view of the aortic catheter 100 taken along line 4—4. The aortic catheter 100 has an elongated catheter shaft 102 having a proximal end 104 and a distal end 106. The elongated catheter shaft 102 should have an overall length sufficient to reach from an arterial insertion point to the patient's ascending aorta. For femoral artery deployment in adult human patients, the elongated catheter shaft 102 preferably has an overall length from approximately 60 to 120 cm, more preferably 70 to 90 cm. The elongated catheter shaft 102 has a proximal portion 1 and a distal portion 2, which are joined together end-to-end, as shown in FIG. 1.

As shown in FIG. 2, which is a magnified lateral cross section of the aortic catheter 100 of FIG. 1 taken along line 2—2, the proximal portion 1 of the catheter shaft 102 has six lumens: a corporeal perfusion lumen 108, an arch perfusion lumen 110, an arch pressure lumen 112, a balloon inflation lumen 114, a guide wire and cardioplegia lumen 116 and a root pressure lumen 118.

As shown in FIG. 3, which is a magnified lateral cross section of the aortic catheter 100 of FIG. 1 taken along line 3—3, five of the six lumens continue into the distal portion 2 of the catheter shaft 102: the arch perfusion lumen 110, the arch pressure lumen 112, the balloon inflation lumen 114, the guide wire and cardioplegia lumen 116 and the root pressure lumen 118. FIG. 4 is a distal view of the distal end 106 taken along line 4-4 showing the root pressure port 134 and the guidewire/cardioplegia port 136.

The distal portion 2 of the catheter shaft 102 preferably has a length of approximately 30 to 60 cm, with the proximal portion 1 making up the remainder of the overall length of the elongated catheter shaft 102. The elongated catheter shaft 102 has an outer diameter which is preferably from approximately 9 to 22 French (3.0–7.3 mm diameter), more preferably from approximately 12 to 18 French (4.0–6.0 mm diameter) for adult human patients. Catheters for pediatric patients may be somewhat smaller. Preferably, the elongated catheter shaft 102 is relatively constant in diameter along its length, as shown in FIG. 1. Alternatively, the proximal portion 1 may be made with an outer diameter somewhat larger than the distal portion 2, with a smoothly tapered transition between the two portions.

It should be noted that, for use in animal models, such as porcine or canine models, the size of the aortic catheter 100 may vary somewhat, depending on the size of the animal subject. In exemplary embodiments intended for use in a porcine model, the aortic catheter 100 was made with a catheter shaft 102 having an outside diameter in one case of 10.5 French (3.5 mm) and in another case of 12 French (4.0 mm) and an overall length of 50–52 cm, a distal portion 2 of 30–34 cm and a proximal portion 1 of 16–22 cm. FIGS. 5 and 6 are full scale drawings of lateral cross sections taken along line 1—1 and line 2—2 in FIG. 1, respectively, showing the actual size of a catheter with a 10.5 French (3.5 mm) outer diameter. FIGS. 7 and 8 are full scale drawings of lateral cross sections taken along line 2—2 and line 3—3 in FIG. 1, respectively, showing the actual size of a catheter with a 12 French (4.0 mm) outer diameter.

The proximal portion 1 and the distal portion 2 of the elongated catheter shaft 102 are preferably formed of a flexible thermoplastic material, a thermoplastic elastomer or a thermoset elastomer. The proximal portion 1 and the distal portion 2 of the catheter shaft 102 may be fabricated separately by known extrusion methods and joined together end-to-end, for example by heat welding or by adhesive bonding. Alternatively, the proximal portion 1 and the distal portion 2 of the catheter shaft 102 may be fabricated by dipping or by composite construction techniques and joined together or the entire catheter shaft 102 may be fabricated integrally. Suitable materials for the elongated catheter shaft 102 include, but are not limited to, polyvinylchloride, polyurethane, polyethylene, polypropylene, polyamides (nylons), polyesters, silicone, latex, and alloys or copolymers thereof, as well as braided, coiled or counterwound wire or filament reinforced composites.

An upstream occlusion member 120 is mounted on the distal portion 2 of the catheter shaft 102 near the distal end 106 of the catheter 100. The upstream occlusion member 120 in this embodiment is in the form of an expandable, inflatable balloon bonded to the catheter shaft 102 by heat welding or with an adhesive. Suitable materials for the inflatable balloon upstream occlusion member 120 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof. In addition, the outer surface of the upstream occlusion member 120 may include a friction increasing coating or texture to increase friction with the aortic wall when deployed. The inflatable balloon upstream occlusion member 120 has a deflated state, in which the diameter of the occlusion member 120 is preferably not much larger than the diameter of the catheter shaft 102, and an inflated state, in which the occlusion member 120 expands to a diameter sufficient to occlude blood flow in the ascending aorta of the patient. For use in adult human patients, the inflatable balloon upstream occlusion member 120 preferably has an inflated outer diameter of approximately 1.5 cm to 5.0 cm. Preferably, the inflatable balloon upstream occlusion member 120 has an inflated length that is not significantly longer than its inflated diameter, or, more preferably, is shorter than its inflated diameter. This shortened inflated profile allows the upstream occlusion member 120 to be easily placed within the ascending aorta between the coronary arteries and the brachiocephalic artery without any danger of inadvertently occluding either.

A downstream anchoring member 122 is mounted on the distal portion 2 of the catheter shaft 102 at a position proximal to and spaced apart from the upstream occlusion member 120. The distance between the upstream occlusion member 120 and the downstream anchoring member 122 is preferably between 3 and 20 cm, more preferably between 8 and 15 cm, and is chosen so that when the aortic catheter 100 is deployed and the upstream occlusion member 120 is positioned within the ascending aorta between the coronary arteries and the brachiocephalic artery, the downstream anchoring member 122 will be positioned in the descending aorta downstream of the left subclavian artery. The downstream anchoring member 122 in this embodiment is in the form of an expandable, inflatable balloon bonded to the catheter shaft 102 by heat welding or with an adhesive. The downstream anchoring member 122 is preferably larger, that is to say, more elongated, than the upstream occlusion member 120. Suitable materials for the inflatable balloon downstream anchoring member 122 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof. In addition, the outer surface of the downstream anchoring member 122 may include a friction increasing coating or texture to increase friction with the aortic wall when deployed.

The inflatable balloon downstream anchoring member 122 has a deflated state, in which the diameter of the anchoring member 122 is preferably not much larger than the diameter of the catheter shaft 102, and an inflated state, in which the anchoring member 122 expands to a diameter sufficient to occlude blood flow in the descending aorta of the patient. For use in adult human patients, the inflatable balloon downstream anchoring member 122 preferably has an inflated outer diameter of approximately 1.5 cm to 5.0 cm and a length of approximately 3.5 cm to 7.5 cm. The more elongated form of the inflatable balloon downstream anchoring member 122 creates greater anchoring friction against the wall of the descending aorta when the downstream anchoring member 122 is inflated in order to prevent migration of the aortic catheter 100 due to pressure gradients within the aorta during perfusion.

The corporeal perfusion lumen 108 extends through the proximal portion 1 of the catheter shaft 102 from the proximal end 104 to one or more corporeal perfusion ports 124 on the exterior of the catheter shaft 102 proximal of the downstream anchoring member 122. The corporeal perfusion lumen 108 terminates and is sealed off proximal to the distal portion 2 of the catheter shaft 102. This allows additional space for the arch perfusion lumen 110 in the distal portion 2 of the catheter shaft 102 for greater fluid flow to the aortic arch. The arch perfusion lumen 110 extends through the catheter shaft 102 from the proximal end 104 to one or more arch perfusion ports 126 on the exterior of the catheter shaft 102 between the upstream occlusion member 120 and the downstream anchoring member 122. Preferably, the arch perfusion lumen 110 makes a smoothly tapered transition where it increases in cross sectional area between the proximal portion 1 and the distal portion 2 of the catheter shaft 102 in order to minimize pumping head loss through the lumen. The arch pressure lumen 110 extends through the catheter shaft 102 from the proximal end 104 to an arch pressure port 128 located between the upstream occlusion member 120 and the downstream anchoring member 122 to monitor pressure in the aortic arch. The balloon inflation lumen 114 extends through the catheter shaft 102 from the proximal end 104 to balloon inflation ports 130 and 132 within the upstream occlusion member 120 and the downstream anchoring member 122, respectively. Thus, the common balloon inflation lumen 114 serves for simultaneous inflation and deflation of both the upstream occlusion member 120 and the downstream anchoring member 122. Alternatively, separate inflation lumens may be provided for independently inflating the upstream occlusion member 120 and the downstream anchoring member 122.

The root pressure lumen 118 extends through the catheter shaft 102 from the proximal end 104 to a root pressure port 134 near the distal end 106 of the catheter shaft 102 to monitor pressure in the aortic root. The guide wire and cardioplegia lumen 116 extends from the proximal end 104 of the catheter shaft 102 to a guide wire/cardioplegia port 136 at the distal end 106 of the catheter shaft 102, distal to the upstream occlusion member 120. Preferably, the distal end 106 of the catheter shaft 102 is smoothly tapered or rounded for easy introduction and to avoid trauma or injury to the aortic wall during insertion or withdrawal of the aortic catheter 100. Preferably, the proximal end 104 of the catheter shaft 102 and each of the lumens are connected to a manifold and appropriate fittings, as will be discussed in more detail below.

Preferably, the aortic catheter 100 includes one or more markers, which may include radiopaque markers and/or sonoreflective markers, to enhance imaging of the aortic catheter 100 using fluoroscopy or ultrasound, such as transesophageal echocardiography (TEE). In this illustrative embodiment, the aortic catheter 100 includes a distal radiopaque marker 138 positioned near the distal end 106 of the catheter shaft 102, an intermediate radiopaque marker 140 positioned near the proximal edge of the upstream occlusion member 120, and a proximal radiopaque marker 142 positioned near the distal edge of the downstream anchoring member 122. Each of the radiopaque markers 138, 140, 142 may be made of a ring of dense radiopaque metal, such as gold, platinum, tantalum, tungsten or alloys thereof, or a ring of a polymer or adhesive material heavily loaded with a radiopaque filler material.

FIGS. 9 through 13 illustrate the shaft portion of a second embodiment of the aortic catheter 200, which is also configured for retrograde deployment via a peripheral artery, such as the femoral artery. FIG. 9 is a side view of the shaft portion of the aortic catheter 200. FIG. 10 is a magnified lateral cross section of the aortic catheter 200 taken along line 10—10 in FIG. 9. FIG. 11 is a magnified distal end view of the aortic catheter 200 taken along line 11—11 in FIG. 9. This second embodiment of the aortic catheter 200 is very similar in materials, construction and dimensions to the first embodiment 100 previously described, with the exception that the corporeal perfusion lumen has been eliminated. The aortic catheter 200 has an elongated catheter shaft 202 having a proximal end 204 and a distal end 206. An upstream occlusion member 220, in the form of an inflatable balloon, is mounted on the catheter shaft 202 near the distal end 206 of the catheter shaft 202 so that it is positioned in the ascending aorta when deployed. A larger, more elongated, inflatable balloon, which serves as a downstream anchoring member 222, is mounted at a position proximal to the upstream occlusion member 220 so that is positioned in the descending aorta when deployed.

As shown in FIG. 10, which is a magnified lateral cross section of the aortic catheter of FIG. 9 taken along line 10—10, the catheter shaft 202 has five lumens: an arch perfusion lumen 210, an arch pressure lumen 212, a balloon inflation lumen 214, a guide wire and cardioplegia lumen 216 and a root pressure lumen 218. The arch perfusion lumen 210 extends through the catheter shaft 202 from the proximal end 204 to one or more arch perfusion ports 226 on the exterior of the catheter shaft 202 between the upstream occlusion member 220 and the downstream anchoring member 222. The arch pressure lumen 212 extends through the catheter shaft 202 from the proximal end 204 to an arch pressure port 228 located between the upstream occlusion member 220 and the downstream anchoring member 222 to monitor pressure in the aortic arch. The balloon inflation lumen 214 extends through the catheter shaft 202 from the proximal end 204 to balloon inflation ports 230 and 232 for simultaneous inflation and deflation of the upstream occlusion member 220 and the downstream anchoring member 222. Alternatively, separate inflation lumens may be provided for independently inflating the upstream occlusion member 220 and the downstream anchoring member 222.

The root pressure lumen 218 extends through the catheter shaft 202 from the proximal end 204 to a root pressure port 234 near the distal end 206 of the catheter shaft 202 to monitor pressure in the aortic root. The guide wire and cardioplegia lumen 216 extends from the proximal end 204 of the catheter shaft 202 to a guide wire/cardioplegia port 236 at the distal end 206 of the catheter shaft 202, distal to the upstream occlusion member 220.

The aortic catheter 200 includes a distal radiopaque marker 238 positioned near the distal end 206 of the catheter shaft 202, an intermediate radiopaque marker 240 positioned near the proximal edge of the upstream occlusion member 220, and a proximal radiopaque marker 242 positioned near the distal edge of the downstream anchoring member 222. The proximal end 204 of the catheter shaft 202 and each of the lumens is connected to a manifold and appropriate fittings, as will be discussed in more detail below.

Preferably, the elongated catheter shaft 202 has an outer diameter which is from approximately 9 to 22 French (3.0–7.3 mm diameter), more preferably from approximately 12 to 18 French (4.0–6.0 mm diameter), and an overall length from approximately 60 to 120 cm, more preferably 70 to 90 cm, for femoral artery deployment in adult human patients. In exemplary embodiments intended for use in a porcine model, the aortic catheter 200 was made with a catheter shaft 202 having an outside diameter in one case of 10.5 French (3.5 mm) and in 10 another case of 12 French (4.0 mm) and an overall length of 50–52 cm. FIG. 12 is a full scale drawing of the lateral cross section taken along line 10—10 in FIG. 9 showing the actual size of a catheter 200 with a 10.5 French (3.5 mm) outer diameter. FIG. 13 is a full scale drawing of the lateral cross section taken along line 10—10 in FIG. 9 showing the actual size of a catheter 200 with a 12 French (4.0 mm) outer diameter.

This second embodiment of the aortic catheter 200 has a number of practical advantages over the first embodiment previously described. The aortic catheter 200 is easier to construct, since the entire length of the catheter shaft 202 can be made of a single piece of extruded tubing. In addition, eliminating the corporeal perfusion lumen from the catheter shaft 202 creates more space for the arch perfusion lumen 212, allowing greater arch perfusion flow for a given diameter of catheter shaft 202. The disadvantage of this variation is that the aortic catheter 200 does not provide any lumen for corporeal perfusion flow. Therefore, a separate contralateral or coaxial arterial cannula would be used with this embodiment of the aortic catheter 200 to supply oxygenated blood to the corporeal circulation.

FIG. 14 shows a side view of an aortic catheter 100 according to the present invention with a catheter shaft 102 configured for retrograde deployment via femoral artery access. The features shown in FIG. 14 are applicable to the first or second embodiment of the aortic catheter previously described, as well as other aortic catheters described herein that are intended for retrograde deployment via femoral artery access. In order to facilitate placement of the aortic catheter 100 and to improve the stability of the catheter 100 in the proper position in the patient's aorta, a distal region 144 of the catheter shaft 102 may be preshaped with a curve to match the internal curvature of the patient's aortic arch. The curved distal region 144 represents a J-shaped curve of approximately 180 degrees of arc with a radius of curvature of approximately 2 to 4 cm to match the typical curvature of the aortic arch in an adult human patient. In addition, the distal end 106 of the catheter may be skewed slightly up out of the plane of the curve to accommodate the forward angulation of the patient's ascending aorta. Additionally, the catheter shaft 102 may be reinforced, particularly in the curved distal region 144, for example with braided or coiled wire, to further improve the stability of the catheter 100 in the proper position in the patient's aorta.

As mentioned above, the proximal end 104 of the catheter shaft 102 is connected to a manifold 150 with fittings for each of the catheter lumens. The corporeal perfusion lumen 108 is connected to a Y-fitting 162 that has a barb connector 152 for connection to a perfusion pump or the like and a luer connector 154, which may be used for monitoring perfusion pressure, for withdrawing fluid samples or for injecting medications or other fluids. Likewise, the arch perfusion lumen 110 is connected to a Y-fitting 164 that has a barb connector 156 for connection to a perfusion pump and a luer connector 158. The arch pressure lumen 112 is connected to a luer connector 160 or other fitting suitable for connection to a pressure monitor. The balloon inflation lumen 114 is connected to a luer connector 166 or other fitting, suitable for connection to a syringe or balloon inflation device. The guide wire and cardioplegia lumen 116 is connected to a three-way Y-fitting 170 that has a barb connector 172 for connection to a cardioplegia infusion pump, a luer connector 174 and a guide wire port 176 with a Touhy-Borst adapter or other hemostasis valve. The root pressure lumen 118 is connected to a luer connector 168 or other fitting, suitable for connection to a pressure monitor. Naturally, the Y-fitting 162 for the corporeal perfusion lumen 108 would be unnecessary for the second embodiment of the aortic catheter 200 described above.

Figure 15:
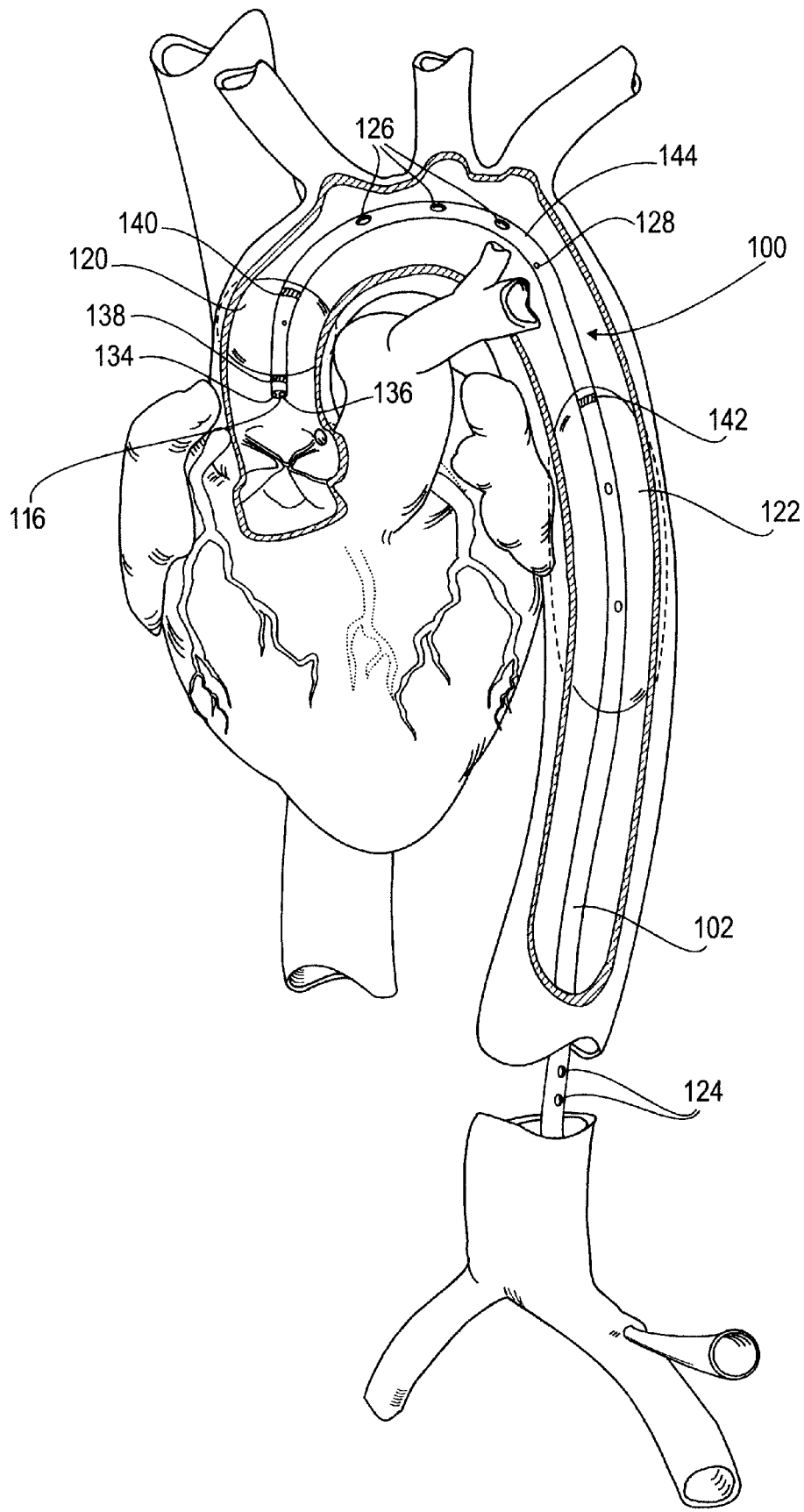
FIG. 15 shows a side view of the aortic catheter according to the present invention with a catheter shaft configured for retrograde deployment via femoral artery access.

FIG. 15 is a schematic diagram showing an aortic catheter 100 according to the present invention deployed within a patient's aorta via femoral artery access. The aortic catheter 100 is introduced into the patient's circulatory system through a peripheral artery access, such as the femoral artery, by the percutaneous Seldinger technique, through an introducer sheath or via an arterial cutdown. In the case of the second embodiment of the aortic catheter 100 described above, the catheter 100 may optionally be introduced into the femoral artery through a coaxial arterial perfusion cannula (not shown). Meanwhile, one or more venous cannulas are introduced into the vena cava via the femoral vein or the jugular vein. The aortic catheter 100 is advanced up the descending aorta and across the aortic arch under fluoroscopic or ultrasound guidance with the aid of a guide wire within the guide wire and cardioplegia lumen 116. The aortic catheter 100 is advanced until the upstream occlusion member 120 is positioned within the ascending aorta between the coronary arteries and the brachiocephalic artery and the downstream anchoring member 122 is positioned in the descending aorta downstream of the left subclavian artery, as evidenced by the radiopaque markers 138, 140, 142, and the guide wire is withdrawn. Using a multihead cardiopulmonary bypass pump or the like, perfusion of oxygenated blood is started through the corporeal perfusion ports 124 (or arterial cannula) and the arch perfusion ports 126 to take some of the pumping load off of the heart. The upstream occlusion member 120 and the downstream anchoring member 122 are then inflated, preferably with saline solution or a mixture of saline and a radiopaque contrast agent, to partition the aorta, whereupon a cardioplegic agent, such as cold crystalloid cardioplegia or blood cardioplegia, is infused through the guide wire and cardioplegia lumen 116 to induce cardioplegic arrest. Perfusion is maintained through the corporeal perfusion ports 124 or arterial cannula and the arch perfusion ports 126 and cardioplegic arrest is maintained by continued infusion of the cardioplegic agent through the guide wire and cardioplegia lumen 116 or via retrograde infusion through a coronary sinus catheter as long as necessary for completion of the surgical procedure using minimally invasive or standard open-chest techniques. Perfusion temperatures, perfusate compositions and flow rates may be optimized to each of the segmented regions of the patient's circulation for optimal organ preservation while on cardiopulmonary bypass. While the aortic catheter 100 is deployed, the downstream anchoring member 122 stabilizes and anchors the catheter shaft 102 and prevents upstream or downstream migration of the catheter 100 or the upstream occlusion member 120 due to differential pressures within the aorta. At the completion of the surgical procedure, the upstream occlusion member 120 and the downstream anchoring member 122 are deflated to allow oxygenated blood to flow into the patient's coronary arteries, whereupon the heart should spontaneously resume normal sinus rhythm. If necessary, cardioversion or defibrillation shocks may be applied to restart the heart. The patient is then weaned off of bypass and the aortic catheter 100 and any other cannulas are withdrawn.

FIGS. 16 through 24 illustrate a third embodiment of the aortic catheter 300 of the present invention, which is configured for antegrade deployment via an aortotomy or direct aortic puncture. FIG. 16 is a side view of the shaft portion of the aortic catheter 300. FIG. 17 is a magnified lateral cross section of the aortic catheter 300 taken along line 17—17 in FIG. 16. FIG. 18 is a magnified lateral cross section of the aortic catheter 300 taken along line 18—18 in FIG. 16. FIG. 19 is a magnified lateral cross section of the aortic catheter 300 taken along line 19—19 in FIG. 16. In many respects this third embodiment of the aortic catheter 300 is similar in materials, construction and dimensions to the first 100 and second 200 embodiments previously described, however because this catheter 300 is configured for antegrade deployment, the proximal and distal positions of many of the features of the catheter are reversed with respect to the retrograde embodiments previously described.

The aortic catheter 300 has an elongated catheter shaft 302 having a proximal end 304 and a distal end 306. Because the aortic catheter 300 is introduced directly into the ascending aorta, the elongated catheter shaft 302 has an overall length of approximately 20 to 60 cm. The elongated catheter shaft 302 has a proximal portion 1, an intermediate portion 2 and a distal portion 3, which are joined together end-to-end, as shown in FIG. 16. As shown in FIG. 17, which is a magnified lateral cross section of the aortic catheter 300 of FIG. 16 taken along line 17—17, the proximal portion 1 of the catheter shaft 302 has four lumens: a guide wire and corporeal perfusion lumen 308, an arch perfusion lumen 310, an arch pressure lumen 312, a balloon inflation lumen 314. As shown in FIG. 18, which is a magnified lateral cross section of the aortic catheter 300 of FIG. 16 taken along line 18—18, two of the four lumens continue into the intermediate portion 2 of the catheter shaft 302: the balloon inflation lumen 314 and the guide wire and corporeal perfusion lumen 308. As shown in FIG. 19, which is a magnified lateral cross section of the aortic catheter 300 of FIG. 16 taken along line 19—19, only the guide wire and corporeal perfusion lumen 308 continue into the distal portion 3 of the catheter shaft 302. The distal portion 3 of the catheter shaft 302 preferably has a length of approximately 2 to 10 cm, the intermediate portion 2 has a length of approximately 2 to 10 cm, with the proximal portion 1 making up the remainder of the overall length of the elongated catheter shaft 302. The elongated catheter shaft 302 has an outer diameter which is preferably from approximately 9 to 22 French (3.0–7.3 mm diameter), more preferably from approximately 12 to 18 French (4.0–6.0 mm diameter) for adult human patients. Catheters for pediatric patients may be somewhat smaller. Preferably, the elongated catheter shaft 302 is relatively constant in diameter along its length, as shown in FIG. 16. Alternatively, the catheter shaft 302 may taper at the transitions between the proximal portion 1, the intermediate portion 2 and the distal portion 3.

In exemplary embodiments intended for use in a porcine model, the aortic catheter 300 was made with a catheter shaft 302 having an outside diameter in one case of 10.5 French (3.5 mm) and in another case of 12 French (4.0 mm) and an overall length of 25–28 cm. FIGS. 20 and 21 are full scale drawings of lateral cross sections taken along line 17—17 and line 18—18 in FIG. 16, respectively, showing the actual size of an aortic catheter 300 with a 10.5 French (3.5 mm) outer diameter. FIGS. 22 and 23 are full scale drawings of lateral cross sections taken along line 1—1 and line 2—2 in FIG. 16, respectively, showing the actual size of an aortic catheter 300 with a 12 French (4.0 mm) outer diameter.

A downstream anchoring member 322, in the form of a large, i.e. elongated, expandable, inflatable balloon, is mounted on the catheter shaft 302 near the distal end 306 of the catheter shaft 302. When inflated, the downstream anchoring member 322 expands to a diameter sufficient to occlude blood flow in the descending aorta. For use in adult human patients, the inflatable balloon downstream anchoring member 322 preferably has an inflated outer diameter of approximately 1.5 cm to 4.0 cm and a length of approximately 3.5 cm to 7.5 cm. An upstream occlusion member 320, in the form of an expandable, inflatable balloon, is mounted on the catheter shaft 302 at a position proximal to and spaced apart from the downstream anchoring member 322 so that it is positioned in the ascending aorta when deployed. The distance between the upstream occlusion member 320 and the downstream anchoring member 322 is preferably between 3 and 20 cm, more preferably between 8 and 15 cm, and is chosen so that, when the aortic catheter 300 is deployed and the upstream occlusion member 320 is positioned within the ascending aorta between the coronary arteries and the brachiocephalic artery, the downstream anchoring member 322 will be positioned in the descending aorta downstream of the left subclavian artery. When inflated, the upstream occlusion member 320 expands to a diameter sufficient to occlude blood flow in the ascending aorta. For use in adult human patients, the inflatable balloon upstream occlusion member 320 preferably has an inflated outer diameter of approximately 1.5 cm to 4.0 cm. Preferably, the inflatable balloon upstream occlusion member 320 has an inflated length that is not significantly longer than its inflated diameter, or, more preferably, is shorter than its inflated diameter to allows the upstream occlusion member 320 to be easily placed within the ascending aorta between the coronary arteries and the brachiocephalic artery without any danger of inadvertently occluding either.

The arch perfusion lumen 310 extends through the catheter shaft 302 from the proximal end 304 to one or more arch perfusion ports 326 on the exterior of the catheter shaft 302 between the upstream occlusion member 320 and the downstream anchoring member 322. The arch pressure lumen 312 extends through the catheter shaft 302 from the proximal end to an arch pressure port 328 located between the upstream occlusion member 320 and the downstream anchoring member 322 to monitor pressure in the aortic arch. The common balloon inflation lumen 314 extends through the catheter shaft 302 from the proximal end 304 to balloon inflation ports 330, 332 within the upstream occlusion member 320 and the downstream anchoring member 322, respectively. Alternatively, separate inflation lumens may be provided for independently inflating the upstream occlusion member 320 and the downstream anchoring member 322. The guide wire and corporeal perfusion lumen 308 extends from the proximal end 304 of the catheter shaft 302 to one or more corporeal perfusion ports 324 and a guide wire port 336 at the distal end 306, distal to the downstream anchoring member 322. The aortic catheter 300 includes a distal radiopaque marker 338 positioned near the distal end 306 of the catheter shaft 302, an intermediate radiopaque marker 340 positioned near the proximal edge of the downstream anchoring member 322, and a proximal radiopaque marker 342 positioned near the distal edge of the upstream occlusion member 320. As this embodiment of the aortic catheter 300 does not include a cardioplegia lumen, a separate cardioplegia needle or catheter would be used with this embodiment to infuse cardioplegia fluid into the aortic root upstream of the upstream occlusion member 320. Alternatively, a cardioplegia lumen with one or more cardioplegia ports could be included in the proximal portion 1 of the catheter shaft 302.

Figure 24:
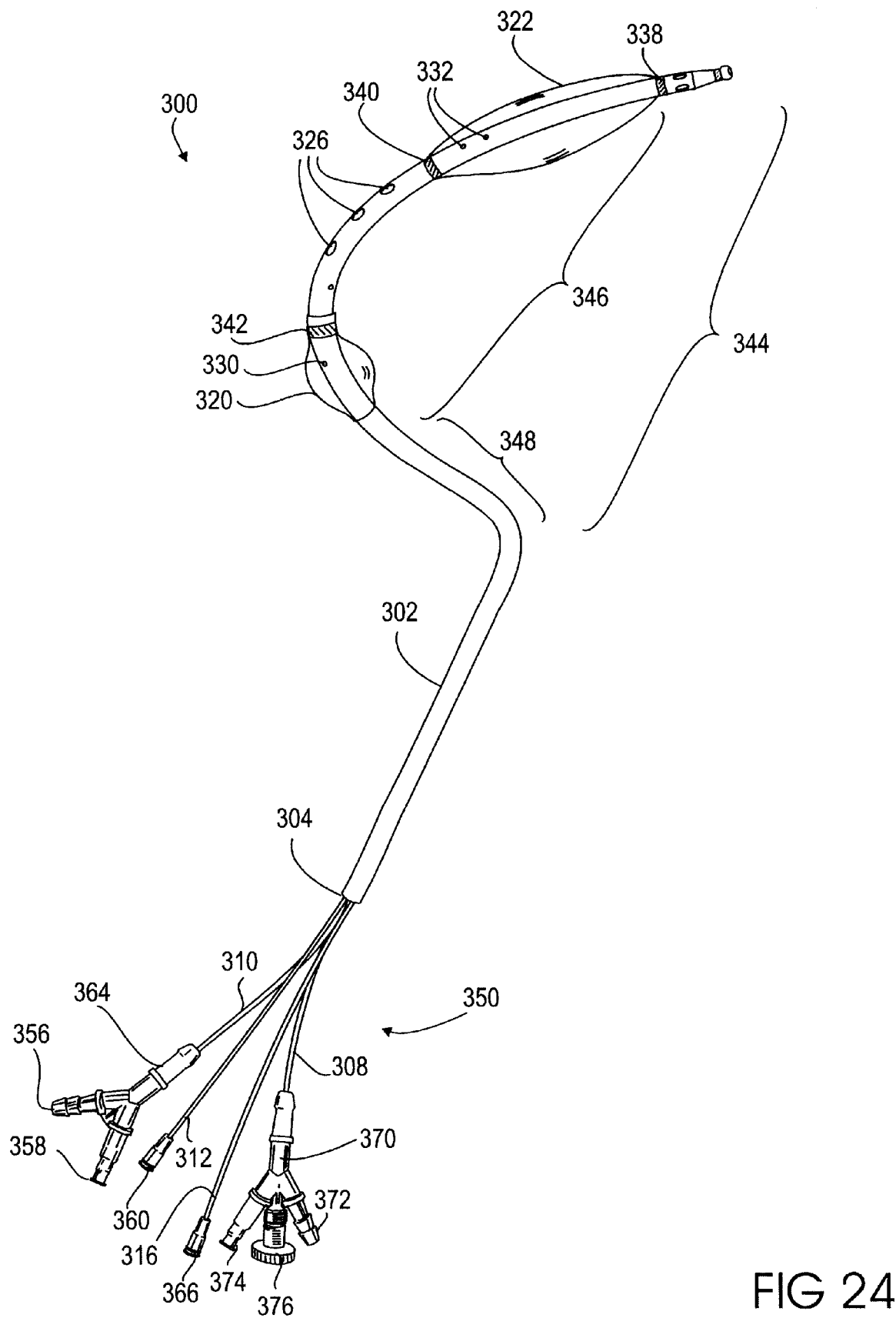
FIG. 24 shows a side view of an aortic catheter according to the present invention with a catheter shaft configured for antegrade deployment via an aortotomy incision in the ascending aorta.

FIG. 24 shows a side view of an aortic catheter 300 according to the present invention with a catheter shaft 302 configured for antegrade deployment via central access through an aortotomy or direct puncture in the ascending aorta. The features shown in FIG. 24 are applicable to the third embodiment of the aortic catheter previously described, as well as other aortic catheters described herein that are intended for antegrade deployment. In order to facilitate placement of the aortic catheter 300 and to improve the stability of the catheter 300 in the proper position in the patient's aorta, a distal region 344 of the catheter shaft 302 may be preshaped with a curve to match the internal curvature of the patient's aortic arch. The curved distal region 344 represents an S-shaped curve with a primary curve 346 of approximately 180 degrees of arc with a radius of curvature of approximately 2 to 4 cm to match the typical curvature of the aortic arch in an adult human patient and a secondary curve 348 that is a bend of approximately 90 degrees or more where the catheter shaft 302 will pass through the aortic wall. Additionally, the catheter shaft 302 may be reinforced, particularly in the curved distal region 344, for example with braided or coiled wire, to further improve the stability of the catheter 300 in the proper position in the patient's aorta.

The proximal end 304 of the catheter shaft 302 is connected to a manifold 350 with fittings for each of the catheter lumens. The arch perfusion lumen 310 is connected to a Y-fitting 364 that has a barb connector 356 for connection to a perfusion pump or the like and a luer connector 358, which may be used for monitoring perfusion pressure, for withdrawing fluid samples or for injecting medications or other fluids.

The arch pressure lumen 312 is connected to a luer connector 360 or other fitting suitable for connection to a pressure monitor. The balloon inflation lumen 314 is connected to a luer connector 366 or other fitting suitable for connection to a syringe or balloon inflation device. The guide wire and corporeal perfusion lumen 308 is connected to a three-way Y-fitting 370 that has a barb connector 372 for connection to a perfusion pump, a luer connector 374 and a guide wire port 376 with a Touhy-Borst adapter or other hemostasis valve. An additional Y-fitting would be necessary if a cardioplegia lumen were included in the aortic catheter 300.

Figure 25:
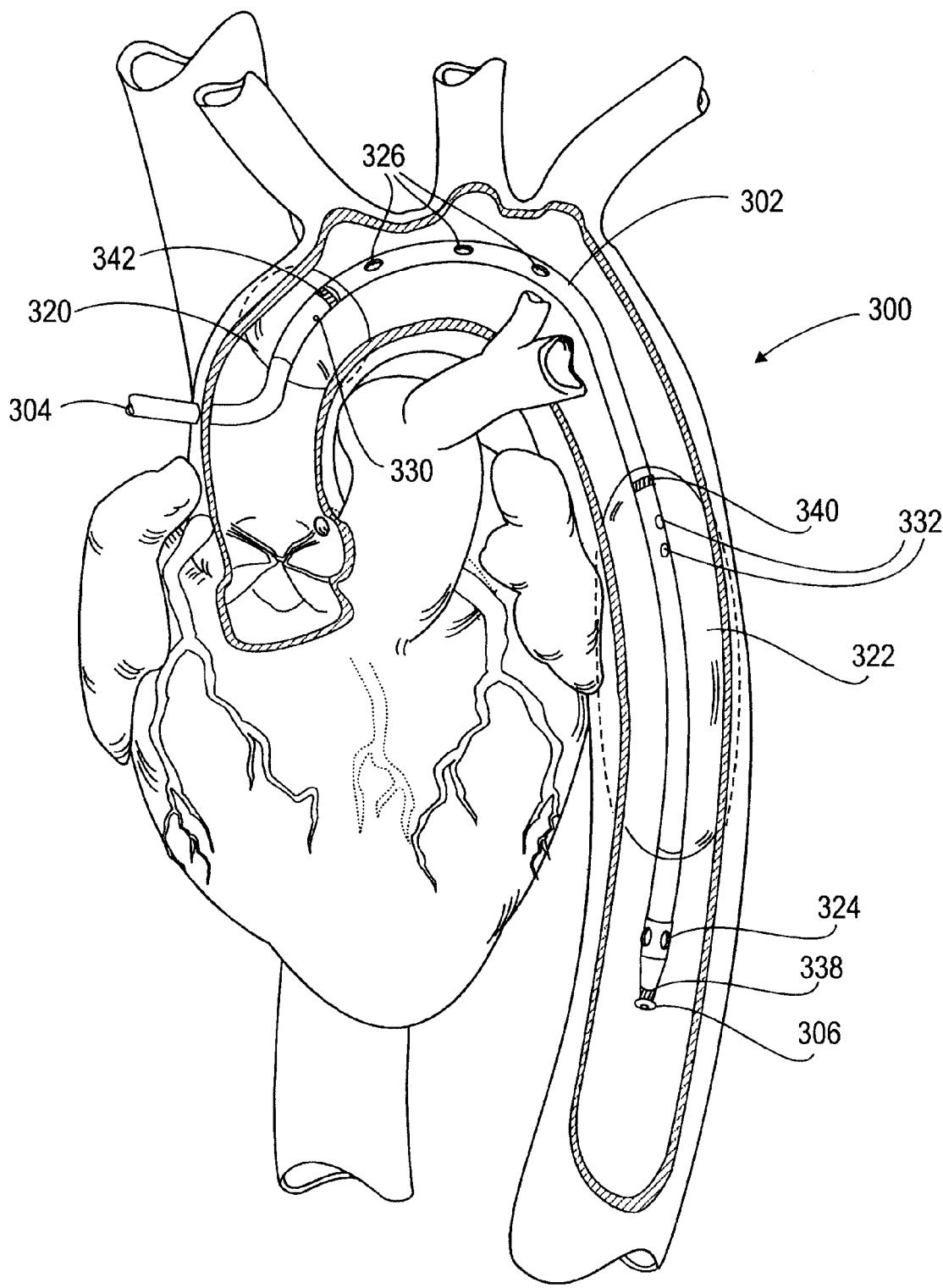
FIG. 25 is a schematic diagram of an aortic catheter according to the present invention, deployed within a patient's aorta via an aortotomy incision in the ascending aorta.

FIG. 25 is a schematic diagram showing an aortic catheter 300 according to the present invention deployed within a patient's aorta via an aortotomy incision in the ascending aorta.

First, the patient's ascending aorta is accessed through a stemotomy, a thoracotomy or using a port-access approach. A purse string suture is placed in the wall of the ascending aorta and an aortotomy incision is made inside of the purse string. Then, the aortic catheter 300 is introduced into the patient's ascending aorta through the aortotomy incision. Meanwhile, one or more venous cannulas are introduced into the vena cava via the femoral vein or the jugular vein. The aortic catheter 300 is advanced up the ascending aorta and across the aortic arch under fluoroscopic or ultrasound guidance, or under direct visualization with the aid of a guide wire within the guide wire and corporeal perfusion lumen 308. The aortic catheter 300 is advanced until the upstream occlusion member 320 is positioned within the ascending aorta between the coronary arteries and the brachiocephalic artery and the downstream anchoring member 322 is positioned in the descending aorta downstream of the left subclavian artery, as evidenced by the radiopaque markers 338, 340, 342, and the guide wire is withdrawn. Using a multihead cardiopulmonary bypass pump or the like, perfusion of oxygenated blood is started through the corporeal perfusion ports 324 and the arch perfusion ports 326 to take some of the pumping load off of the heart. The upstream occlusion member 320 and the downstream anchoring member 322 are then inflated to partition the aorta, whereupon a cardioplegic agent, such cold crystalloid cardioplegia or blood cardioplegia, is infused through a separate cardioplegia needle or catheter placed in the aortic root upstream of the upstream occlusion member 320 (or through the optional cardioplegia lumen) to induce cardioplegic arrest. Perfusion is maintained through the corporeal perfusion ports 324 and the arch perfusion ports 326 and cardioplegic arrest is maintained by continued infusion of the cardioplegic agent through the cardioplegia needle or catheter or via retrograde infusion through a coronary sinus catheter as long as necessary for completion of the surgical procedure using minimally invasive or standard open-chest techniques. Perfusion temperatures, perfusate compositions and flow rates may be optimized to each of the segmented regions of the patient's circulation for optimal organ preservation while on cardiopulmonary bypass. While the aortic catheter 300 is deployed, the downstream anchoring member 322 stabilizes and anchors the catheter shaft 302 and prevents upstream or downstream migration of the catheter 300 or the upstream occlusion member 320 due to differential pressures within the aorta. At the completion of the surgical procedure, the upstream occlusion member 320 and the downstream anchoring member 322 are deflated to allow oxygenated blood to flow into the patient's coronary arteries, whereupon the heart should spontaneously resume normal sinus rhythm. If necessary, cardioversion or defibrillation shocks may be applied to restart the heart. The patient is then weaned off of bypass and the aortic catheter 300 and any other cannulas are withdrawn.

FIGS. 26 through 30 show several alternate embodiments of the aortic catheter of the present invention illustrating some of the variations possible for the upstream occlusion member and the downstream anchoring member. These variations are equally applicable to catheters configured for retrograde deployment via peripheral artery access or for antegrade deployment via an aortotomy incision in the ascending aorta. The exact configurations of the embodiments shown are illustrative of only a few of the many possible variations of the aortic catheter of the present invention and therefore should not be considered as limiting examples.

Figure 26:
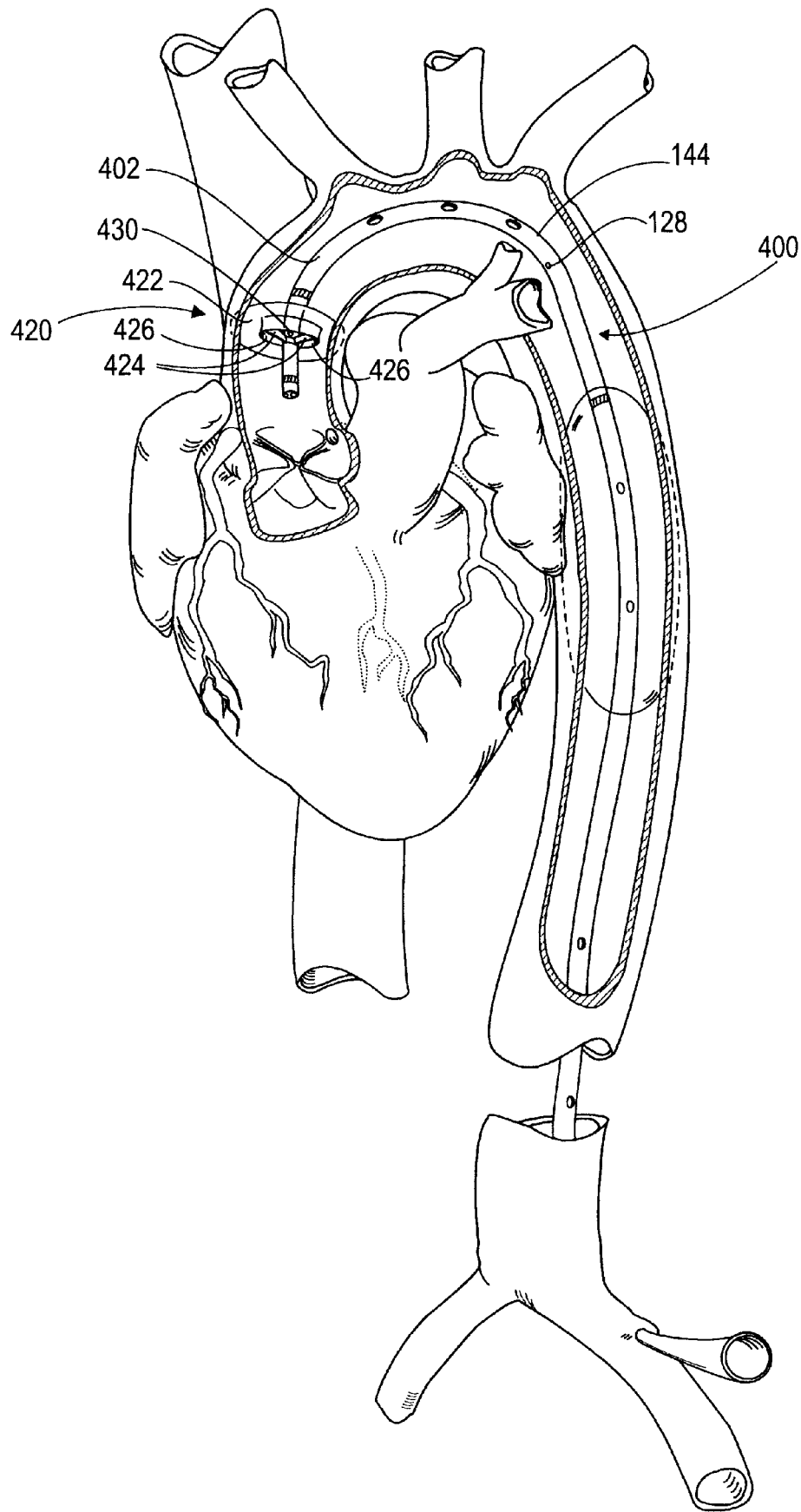
FIG. 26 is a schematic diagram showing a fourth embodiment of the aortic catheter, having an upstream occlusion member in the form of a narrow, disk-shaped balloon, deployed within a patient's aorta via femoral artery access.

FIG. 26 is a schematic diagram showing a fourth embodiment of the aortic catheter 400 of the present invention deployed within a patient's aorta via femoral artery access. In many respects this fourth embodiment of the aortic catheter 400 is similar in materials, construction and dimensions to the first 100 and second 200 embodiments previously described, with the exception that the upstream occlusion member 420 is in the form of a narrow, disk-shaped balloon. In this embodiment, the narrow, disk-shaped balloon upstream occlusion member 420 is formed with an outer toroidal section 422 joined to the catheter shaft 402 by a web 426. One or more spoke-like radial inflation passages 424 connect the inflation port or ports 430 on the catheter shaft 402 with the outer toroidal section 422. When inflated, the outer toroidal section 422 of the upstream occlusion member 420 expands to a diameter sufficient to occlude blood flow in the ascending aorta. For use in adult human patients, the upstream occlusion member 420 preferably has an inflated outer diameter of approximately 1.5 to 4.0 cm. One manner of fabricating the upstream occlusion member 420 is by making a roughly spherical or disk-shaped balloon preform by known balloon forming techniques, then joining sectors of the proximal and distal surface of the balloon preform to one another by heat welding or adhesive bonding to form a web 426, leaving open radial inflation passages 424 connected to the outer toroidal section 422. Other suitable processes for fabricating the upstream occlusion member 420 include dip molding the upstream occlusion member 420 on a positive mold using a lost wax process and slurry molding or rotational molding the upstream occlusion member 420 in a negative mold. Suitable materials for the inflatable balloon upstream occlusion member 420 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof. In addition, the outer surface of the upstream occlusion member 420 may include a friction increasing coating or texture to increase friction with the aortic wall when deployed. The narrow, disk-shaped profile of the upstream occlusion member 420 allows it to be easily placed within the ascending aorta between the coronary arteries and the brachiocephalic artery without any danger of inadvertently occluding either. As noted above, this embodiment may also be configured for antegrade deployment via an aortotomy incision in the ascending aorta, similar to the third embodiment 300 previously described.

Figure 27:
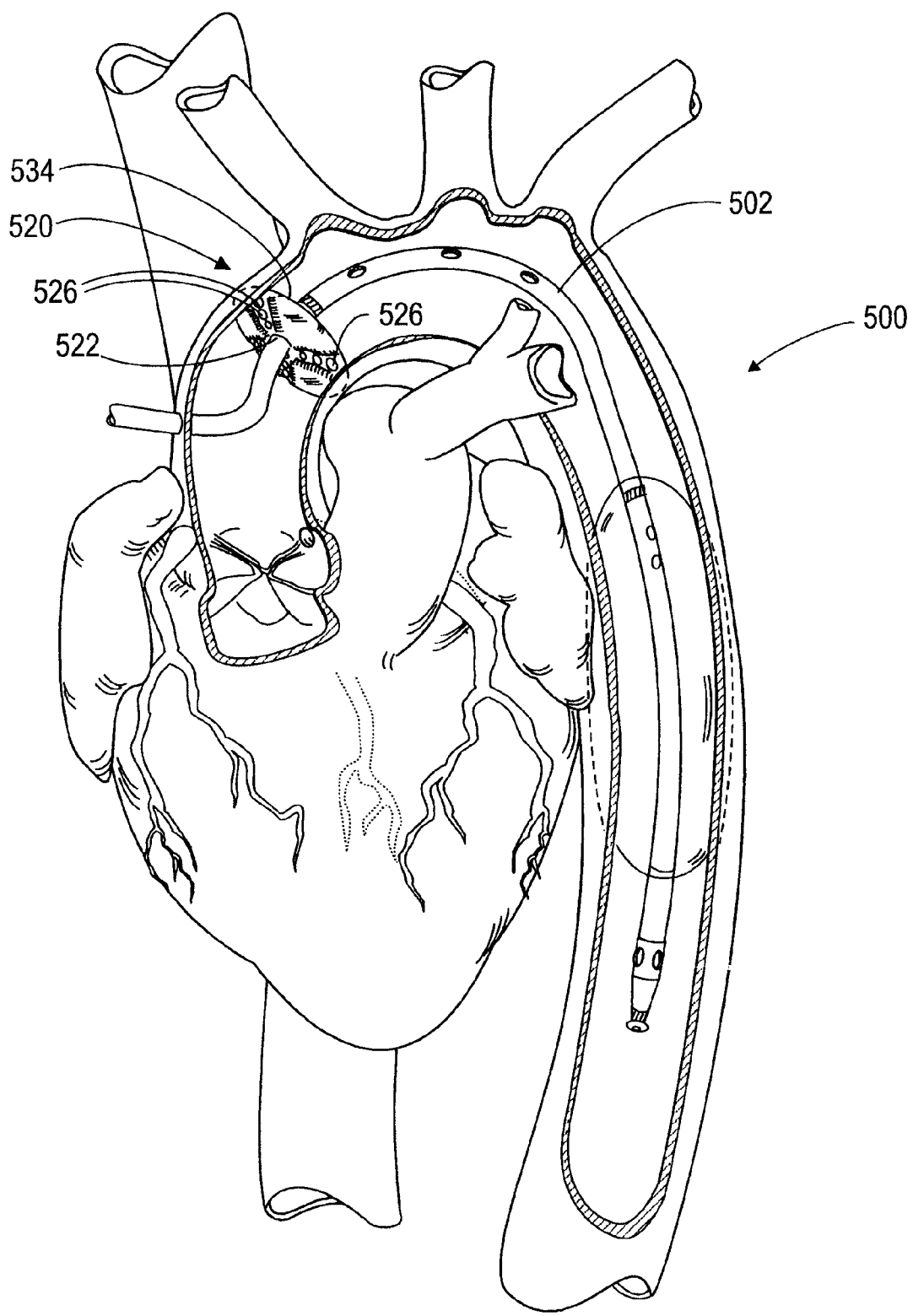
FIG. 27 is a schematic diagram showing a fifth embodiment of the aortic catheter, having an upstream occlusion member in the form of a narrow, disk-shaped balloon, deployed within a patient's aorta via an aortotomy incision in the ascending aorta.

FIG. 27 is a schematic diagram showing a fifth embodiment of the aortic catheter 500 of the present invention deployed within a patient's aorta via an aortotomy incision in the ascending aorta. In many respects this fifth embodiment of the aortic catheter 500 is similar in materials, construction and dimensions to the third 300 embodiment previously described, with the exception that the upstream occlusion member 520 is in the form of a narrow, disk-shaped balloon. In this embodiment, the narrow, disk-shaped balloon upstream occlusion member 520 has an upstream surface 522 and a downstream surface 534 that are joined to one another at a multiplicity of adhesion points 526 in a quilt-like pattern.

The adhesion points 526 may be formed by heat welding or adhesive bonding or the occlusion member 520 may have an internal structure such as fibers or other connecting members joining the upstream surface 522 to the downstream surface 534. The quilt-like pattern of adhesion points 526 allows the occlusion member 520 to maintain its narrow, disk-shaped profile when inflated. When inflated, the upstream occlusion member 520 expands to a diameter sufficient to occlude blood flow in the ascending aorta, preferably between approximately 1.5 and 4.0 cm. Suitable materials for the inflatable balloon upstream occlusion member 520 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof. In addition, the outer surface of the upstream occlusion member 520 may include a friction increasing coating or texture to increase friction with the aortic wall when deployed. The narrow, disk-shaped profile of the upstream occlusion member 520 allows it to be easily placed within the ascending aorta between the coronary arteries and the brachiocephalic artery without any danger of inadvertently occluding either. As noted above, this embodiment may also be configured for retrograde deployment via peripheral artery access, similar to the first 100 or second 200 embodiments previously described.

Figure 28:
FIG. 28 is a schematic diagram showing a sixth embodiment of the aortic catheter, having an upstream occlusion member in the form of a selectively deployable peripheral flow external catheter valve, deployed within a patient's aorta via femoral artery access.

FIG. 28 is a schematic diagram showing a sixth embodiment of the aortic catheter 600, having an upstream occlusion member 620 in the form of a selectively deployable peripheral flow external catheter valve, deployed within a patient's aorta via femoral artery access. As noted above, this embodiment may also be configured for antegrade deployment via an aortotomy incision in the ascending aorta. In this exemplary embodiment, the upstream occlusion member 620 would preferably be in the form of an antegrade, peripheral flow valve, as described in commonly owned, patent application Ser. No. 08/665,635, and co owned U.S. Pat. Nos., 5,827,237 and 5,833,671, which have previously been incorporated by reference. The peripheral flow valve upstream occlusion member 620 is constructed with one or more valve leaflets 622 pivotally attached to the catheter shaft 602. The leaflets 622 of the peripheral flow valve 620 tend to pivot outward to seal against the wall of the ascending aorta in response to positive perfusion pressure in the aortic arch downstream of the occlusion member 620. Alternatively or in addition to this passive valve action, the peripheral flow valve upstream occlusion member 620 may be actively deployed by one or more actuation wires (not shown) extending through the elongated catheter shaft 602 and attached to the valve leaflets 622.

Figure 29:
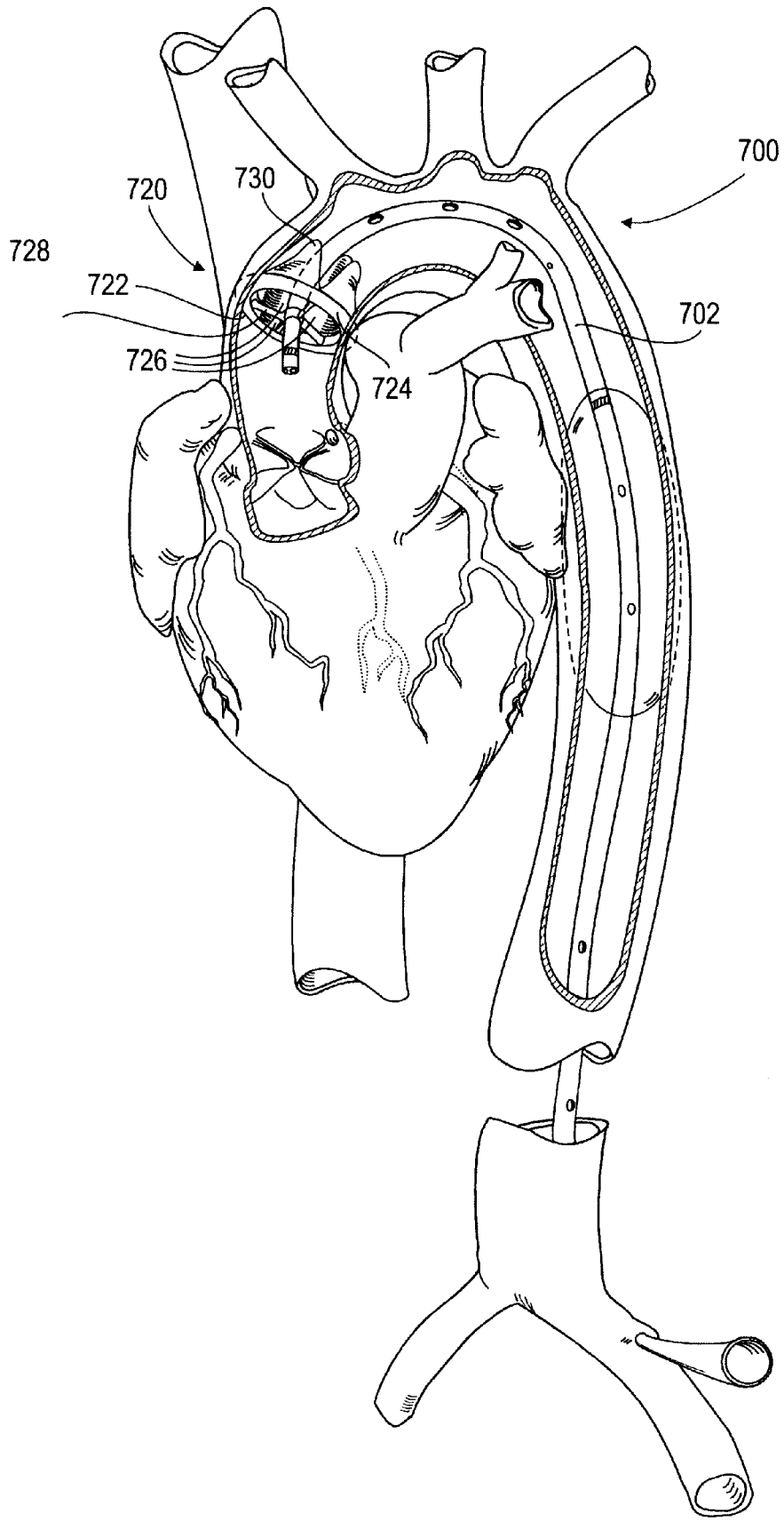
FIG. 29 is a schematic diagram showing a seventh embodiment of the aortic catheter, having an upstream occlusion member in the form of a selectively deployable central flow external catheter valve deployed within a patient's aorta via femoral artery access.

FIG. 29 is a schematic diagram showing a seventh embodiment of the aortic catheter 700, having an upstream occlusion member 720 in the form of a selectively deployable central flow external catheter valve deployed within a patient's aorta via femoral artery access. As noted above, this embodiment may also be configured for antegrade deployment via an aortotomy incision in the ascending aorta. In this exemplary embodiment, the upstream occlusion member 720 would preferably be in the form of an antegrade, central flow valve, as described in in commonly owned, patent application Ser. No. 08/665,635, and co owned U.S. Pat. No. , 5,827,237 and 5,833,671, which have previously been incorporated by reference. The central flow valve upstream occlusion member 720 is constructed with a selectively expandable skeleton structure 722 that is mounted on the catheter shaft 702. In one preferred embodiment, the skeleton structure 722 has an inflatable outer rim 724 supported on the catheter shaft 702 by a plurality of inflatable radial spokes 726. Between the inflatable outer rim 724 and radial spokes 726 are a plurality of flow fenestrations 728. One or more valve leaflets 730 (shown in the open position for clarity) are pivotally attached to the outer rim 724 or the radial spokes 726 of the skeleton structure 722. The leaflets 730 of the central flow valve tend to pivot inward to seal the flow fenestrations 728 in response to positive perfusion pressure in the aortic arch downstream of the occlusion member 720. Alternatively or in addition to this passive valve action, the central flow valve upstream occlusion member 720 may be actively deployed by one or more actuation wires (not shown) extending through the elongated catheter shaft 702 and attached to the valve leaflets 730.

Figure 30:
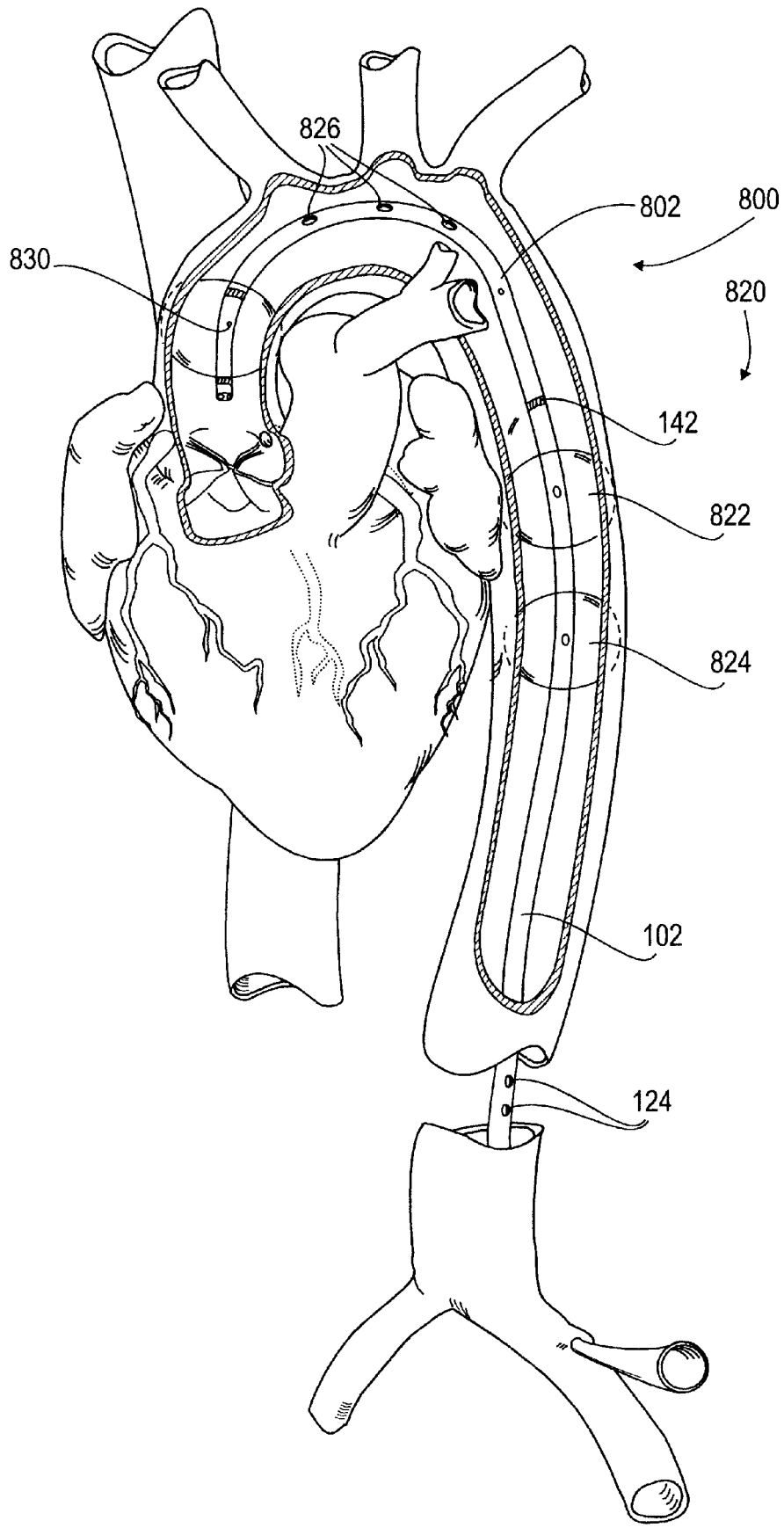
FIG. 30 is a schematic diagram showing an eighth embodiment of the aortic catheter, having a downstream anchoring member in the form of two inflatable balloons, deployed within a patient's aorta via femoral artery access.

FIG. 30 is a schematic diagram showing an eighth embodiment of the aortic catheter 800, having a downstream anchoring member 820 in the form of two inflatable balloons 822, 824, deployed within a patient's aorta via femoral artery access. In many respects this eighth embodiment of the aortic catheter 800 is similar in materials, construction and dimensions to the first 100 and second 200 embodiments previously described, with the exception that the downstream anchoring member 820 is constructed in the form of two or more inflatable balloons 822, 824 as another means to achieve the elongated geometry of the downstream anchoring member in the embodiments previously described. Each of the inflatable balloons 822, 824 is approximately spherical in profile with an inflated diameter sufficient to occlude blood flow in the descending aorta, preferably between approximately 1.5 and 4.0 cm. Suitable materials for the inflatable balloons 822, 824 of the downstream anchoring member 820 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof. In addition, the outer surface of the inflatable balloons 822, 824 may include a friction increasing coating or texture to increase friction with the aortic wall when deployed. Using a plurality of inflatable balloons 822, 824 in the downstream anchoring member 820 has the advantages of greater inflation strength, greater dimensional stability and greater resistance to axial movement of the catheter shaft 802 with respect to the downstream anchoring member 820 when deployed. As noted above, this embodiment may also be configured for antegrade deployment via an aortotomy incision in the ascending aorta, similar to the third embodiment 300 previously described.

What is claimed is:

1. An aortic catheter comprising:
    an elongated catheter shaft configured for introduction into a patient's aorta and having a proximal end and a distal end;
    an upstream occlusion member having an expanded diameter sufficient to block blood flow through the aorta; and
    a downstream anchoring member sized and configured to have a length greater than its diameter and adapted to stabilize the position of the aortic catheter within the aorta.

2. The aortic catheter of claim 1, wherein said upstream occlusion member and said downstream anchoring member are positioned on said elongated catheter shaft such that, when said elongated catheter shaft is introduced into the patient's aorta, said upstream occlusion member is positioned in the ascending aorta between the coronary arteries and the brachiocephalic artery and said downstream anchoring member is positioned in the descending aorta, downstream of the aortic arch.

3. The aortic catheter of claim 2, further comprising an arch perfusion lumen extending through said elongated catheter shaft from said proximal end to at least one arch perfusion port on said elongated catheter shaft between said upstream occlusion member and said downstream anchoring member.

4. The aortic catheter of claim 3, further comprising an arch pressure lumen extending through said elongated catheter shaft from said proximal end to an arch pressure port on said elongated catheter shaft between said upstream occlusion member and said downstream anchoring member.

5. The aortic catheter of claim 2, further comprising a corporeal perfusion lumen extending through said elongated catheter shaft from said proximal end to at least one corporeal perfusion port on said elongated catheter shaft downstream of said upstream occlusion member and said downstream anchoring member.

6. The aortic catheter of claim 2, further comprising a cardioplegia lumen extending through said elongated catheter shaft from said proximal end to at least one cardioplegia port on said elongated catheter shaft upstream of said upstream occlusion member and said downstream anchoring member.

7. The aortic catheter of claim 6, further comprising a root pressure lumen extending through said elongated catheter shaft from said proximal end to a root pressure port on said elongated catheter shaft upstream of said upstream occlusion member and said downstream anchoring member.

8. The aortic catheter of claim 1, wherein said upstream occlusion member is an expandable, inflatable balloon.

9. The aortic catheter of claim 8, further comprising a balloon inflation lumen extending through said elongated catheter shaft from said proximal end to a balloon inflation port on said elongated catheter shaft within said expandable, inflatable balloon.

10. The aortic catheter of claim 1, wherein said upstream occlusion member is a narrow disk-shaped inflatable balloon.

11. The aortic catheter of claim 1, wherein said upstream occlusion member is a peripheral flow external catheter valve.

12. The aortic catheter of claim 1, wherein said upstream occlusion member is a central flow external catheter valve.

13. The aortic catheter of claim 1, wherein said downstream anchoring member is an elongated, expandable, inflatable balloon.

14. The aortic catheter of claim 13, further comprising a balloon inflation lumen extending through said elongated catheter shaft from said proximal end to a balloon inflation port on said elongated catheter shaft within said elongated, expandable, inflatable balloon.

15. The aortic catheter of claim 1, wherein said downstream anchoring member comprises a plurality of inflatable balloons.

16. The aortic catheter of claim 1, wherein said elongated catheter shaft is configured for introduction into the patient's aorta via a peripheral artery access.

17. The aortic catheter of claim 1, wherein said elongated catheter shaft is configured for introduction into the patient's aorta via femoral artery access.

18. The aortic catheter of claim 17, wherein said elongated catheter shaft has a distal region with a curve configured to match an internal curvature of the patient's aortic arch.

19. The aortic catheter of claim 1, wherein said elongated catheter shaft is configured for introduction into the patient's aorta via an aortotomy incision in the ascending aorta.

20. The aortic catheter of claim 19, wherein said elongated catheter shaft has a distal region with a curve configured to match an internal curvature of the patient's aortic arch.

21. The aortic catheter of claim 1, wherein said upstream occlusion member is a first inflatable balloon having a first length; and said downstream anchoring member is a second inflatable balloon having a second length, wherein said second length is greater than said first length.

22. The aortic catheter of claim 21, wherein said first length is less than said expanded diameter of said upstream occlusion member.

23. A method comprising:
   introducing an aortic catheter into a patient's aorta, the aortic catheter having an elongated catheter shaft with a proximal end and a distal end, an upstream occlusion member and a downstream anchoring member, said downstream anchoring member sized and configured to have a length greater than its diameter and adapted to stabilize the position of the aortic catheter in a patient's aorta;
   expanding said upstream occlusion member in the ascending aorta between the coronary arteries and the brachiocephalic artery and expanding said downstream anchoring member in the descending aorta, downstream of the aortic arch; and
   perfusing the patient's aortic arch with fluid through an arch perfusion lumen extending through said elongated catheter shaft from said proximal end to at least one arch perfusion port on said elongated catheter shaft between said upstream occlusion member and said downstream anchoring member.

24. The method of claim 23, further comprising perfusing the patient's descending aorta with fluid through a corporeal perfusion lumen extending through said elongated catheter shaft from said proximal end to at least one corporeal perfusion port on said elongated catheter shaft downstream of said upstream occlusion member and said downstream anchoring member.

25. The method of claim 23, further comprising inducing cardioplegic arrest by infusing a cardioplegic agent through a cardioplegia lumen extending through said elongated catheter shaft from said proximal end to at least one cardioplegia port on said elongated catheter shaft upstream of said upstream occlusion member and said downstream anchoring member.

* * * * *

UNITED STATES PATENT AND TRADEMARK OFFICE
CERTIFICATE OF CORRECTION

PATENT NO. : 6,117,105
DATED : September 12, 2000
INVENTOR(S) : Bresnahan et al.

It is certified that error appears in the above-identified patent and that said Letters Patent is hereby corrected as shown below:

<u>Title page,</u>
Item [12], replace "Bresnaham et al." with -- Bresnahan et al. --.
Item [75], replace "John F. Bresnaham" with -- John F. Bresnahan --.

Signed and Sealed this

Twenty-fourth Day of February, 2004

JON W. DUDAS
*Acting Director of the United States Patent and Trademark Office*